(12) United States Patent
Chang et al.

(10) Patent No.: US 9,186,490 B2
(45) Date of Patent: Nov. 17, 2015

(54) SKIN TREATMENT DEVICE

(71) Applicants: Franklin J. Chang, San Gabriel, CA (US); Henry Ping Chang, San Marino, CA (US)

(72) Inventors: Franklin J. Chang, San Gabriel, CA (US); Henry Ping Chang, San Marino, CA (US)

( * ) Notice: Subject to any disclaimer, the term of this patent is extended or adjusted under 35 U.S.C. 154(b) by 0 days.

(21) Appl. No.: 13/925,857

(22) Filed: Jun. 25, 2013

(65) Prior Publication Data

US 2014/0378887 A1    Dec. 25, 2014

(51) Int. Cl.
| | |
|---|---|
| *A61M 35/00* | (2006.01) |
| *A61N 1/04* | (2006.01) |
| *A61N 1/32* | (2006.01) |
| *A61M 37/00* | (2006.01) |
| *A61B 18/00* | (2006.01) |
| *A61B 17/00* | (2006.01) |
| *A61B 17/32* | (2006.01) |
| *A61B 17/54* | (2006.01) |

(52) U.S. Cl.
CPC ............... *A61M 35/00* (2013.01); *A61M 37/00* (2013.01); *A61N 1/0412* (2013.01); *A61N 1/0472* (2013.01); *A61N 1/327* (2013.01); *A61B 17/545* (2013.01); *A61B 2017/00761* (2013.01); *A61B 2017/320004* (2013.01); *A61B 2018/00452* (2013.01); *A61M 2037/0007* (2013.01); *A61M 2037/0023* (2013.01); *A61N 1/325* (2013.01); *A61N 1/328* (2013.01)

(58) Field of Classification Search
CPC ....... A61N 1/30; A61N 1/325; A61N 1/0472; A61N 1/327; A61N 1/0412; A61M 35/00; A61M 35/003; A61M 2037/0007; A61B 2018/00994
USPC ........... 606/131; 604/289–290; 607/120, 148, 607/153
See application file for complete search history.

(56) References Cited

U.S. PATENT DOCUMENTS

| | | | |
|---|---|---|---|
| 6,171,275 B1 * | 1/2001 | Webster, Jr. .................... | 604/20 |
| 2007/0156124 A1 * | 7/2007 | Ignon et al. ....................... | 606/9 |
| 2010/0049177 A1 * | 2/2010 | Boone et al. ...................... | 606/9 |
| 2011/0046539 A1 * | 2/2011 | Atanasoska et al. ........... | 604/20 |
| 2013/0345661 A1 * | 12/2013 | Chang ........................... | 604/501 |

* cited by examiner

*Primary Examiner* — Theodore Stigell
*Assistant Examiner* — Benjamin Koo

(57) ABSTRACT

A skin treatment device includes a handle and a tip, having a skin applying surface, detachably coupled to the handle. A fluid delivery structure is formed at skin applying surface and has an aperture and a vacuum entry port. A fluid detouring path is defined between the aperture and the vacuum entry port for prolonging a traveling path of fluid from the aperture and the vacuum entry port. An abrading structure, an electrode structure, and a micro-needling structure are selectively provided at the skin applying surface with the fluid delivery structure to provide multiple functions of the tip.

3 Claims, 16 Drawing Sheets

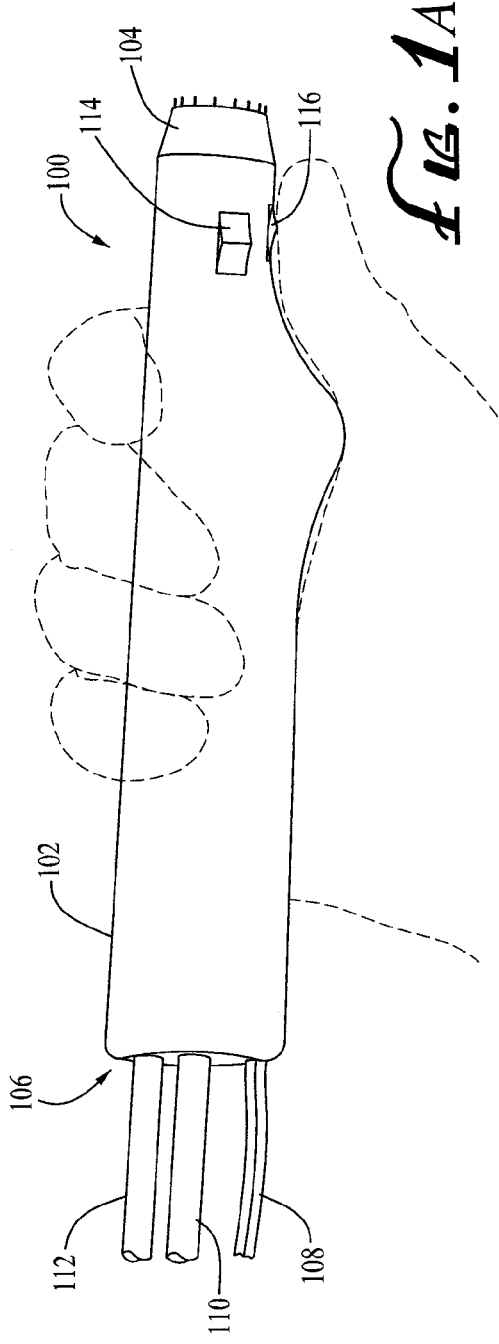
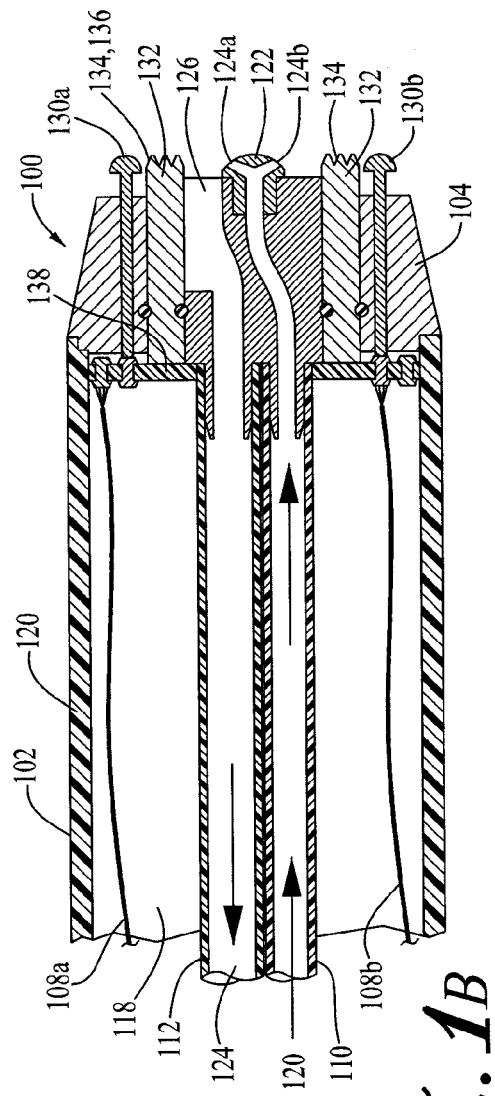

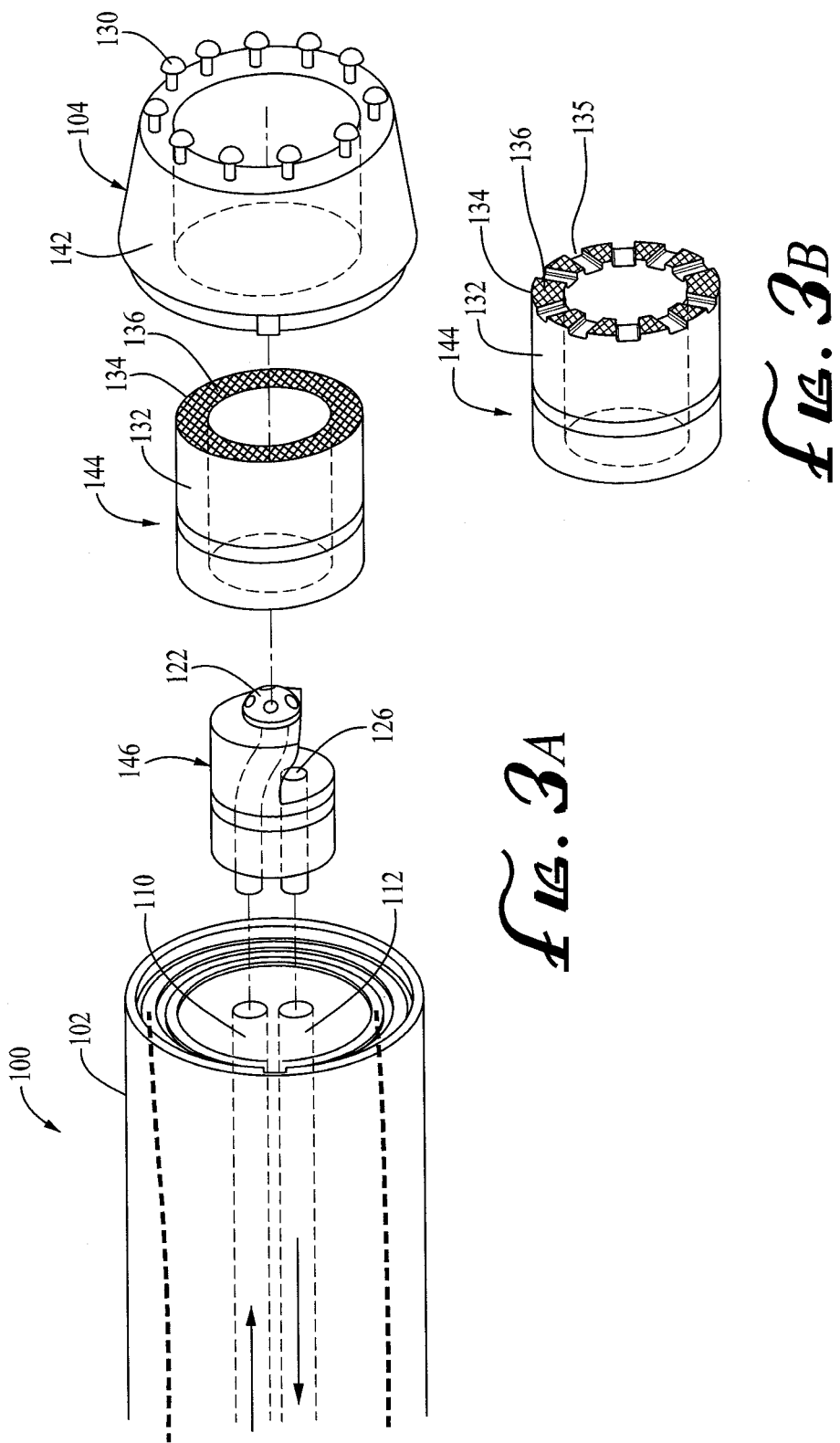

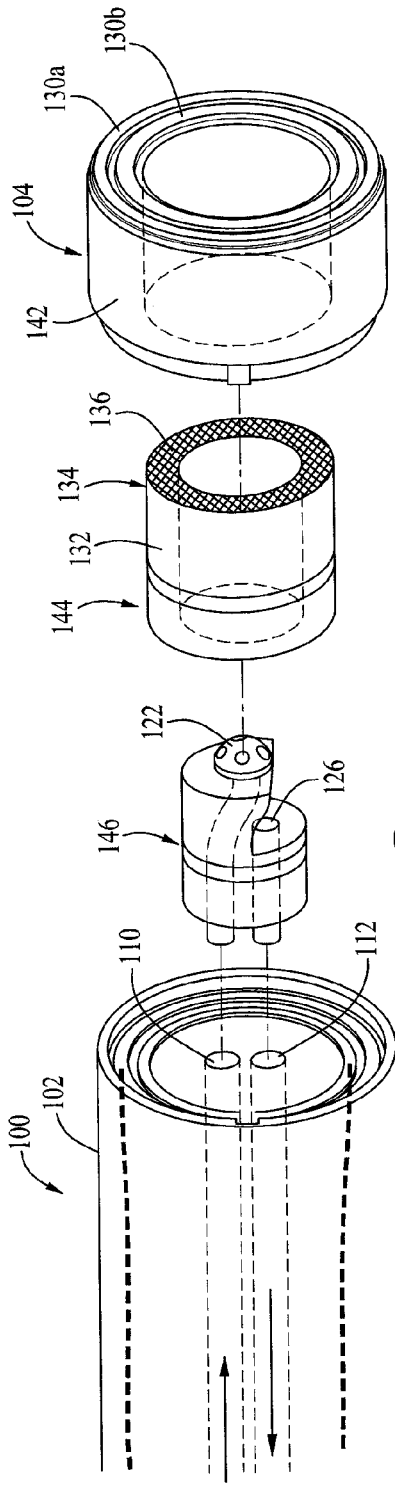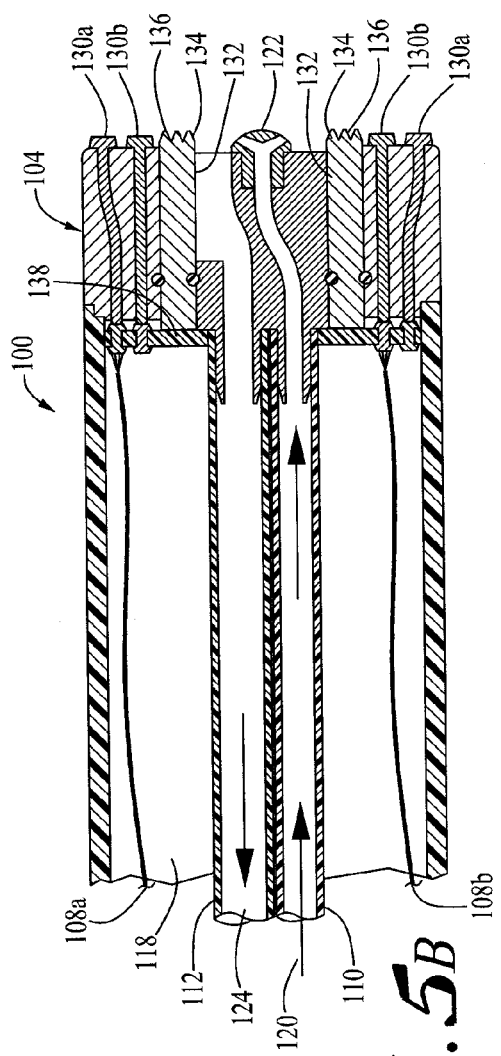

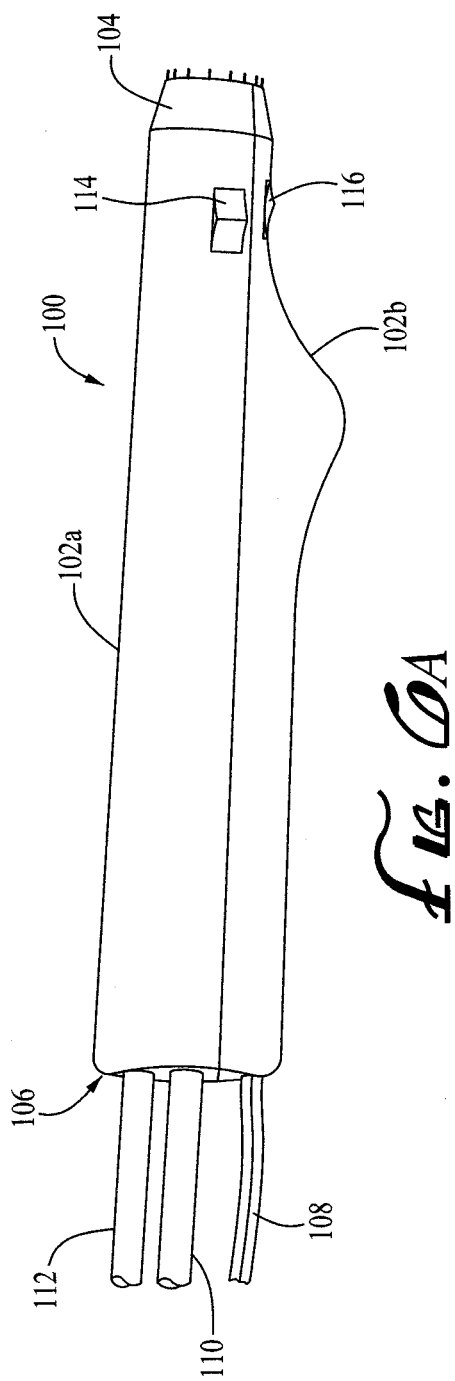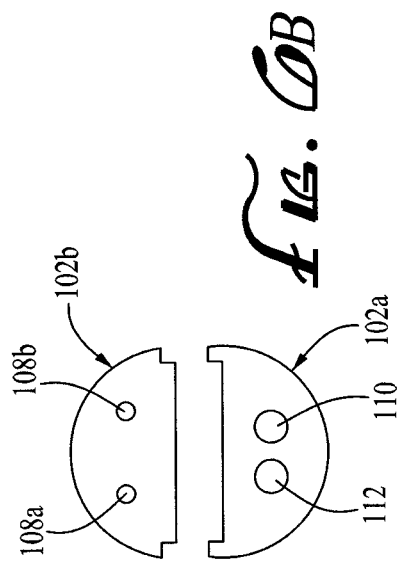

SKIN TREATMENT DEVICE

CROSS REFERENCE WITH RELATED APPLICATION

This is a continuation-in-part application that claims the benefit of priority under 35 U.S.C. §119 of a non-provisional application Ser. No. 13/683,995 and filed Nov. 21, 2012, which is a continuation application of a non-provisional application Ser. No. 13/533,719 and filed Jun. 26, 2012.

BACKGROUND

1. Field of the Invention

The present invention relates to a skin treatment tool. More particularly, the present invention relates to a microdermabrasion device with replaceable tips.

2. Discussion of the Related Art

Current techniques for superficial skin resurfacing, known as microdermabrasion, treat the outer epidermal layer of the skin by removing the superficial layer to induce the body's own natural wound healing response. It is known in the art to couple microdermabrasion with fluid delivery to enhance therapeutic effects. However, combined microdermabrasion/fluid delivery treatments are hindered by the protective barrier function of the stratum corneum which limits the depth of penetration and absorption to the surface of the skin when drugs and/or fluids are applied to the skin.

Other techniques for skin enhancing include transversal drug delivery employing an electrical current (e.g., skin electroporation) are known. However, these techniques have limited results based on: 1) the lack of an efficient fluid supply/return system using a vacuum; 2) the impedance of the stratum corneum which limits the efficacy of the current technologies of electrical penetration of drugs and/or fluids; and 3) the optimal permeation structure of the skin occurs during application of an electrical current and only lasts a few seconds after application of the electrical pulse.

Known technologies for delivery of an electro-current to the skin suffer from one or more of the following deficiencies which lead to the limited results, including, lack an efficient fluid supply/return using a vacuum; an inability to simultaneously apply fluid and electro-current to the skin; and means to lower the impedance of the stratum corneum.

Accordingly, there is a need for a skin resurfacing and enhancement system with enhanced fluid delivery/fluid return capacity which also improves the permeation structure of the skin.

BRIEF SUMMARY OF THE INVENTION

According to the present invention, devices and methods for a combination treatment of the top and bottom layer of a skin surface are described. The device comprises transdermal drug and/or fluid delivery with electrodes providing electric current to stimulate the skin, and an abrasive tip to peel the top layer of skin simultaneously applied to the skins surface. According to one embodiment of the present invention, a skin treatment device that combines a fluid delivery system, an abrasive tip, and an electric current delivery probe in one handle is described. Preferably the device further comprises a vacuum source for removal of fluid and skin debris from the surface of the skin.

The device and methods described herein allow for the simultaneous deep penetration of fluid through the skin by applying an electric current and an abrasive media in the working end of the device to increase skin's permeability. According to alternate embodiments, techniques known as electroporation, ultrasound, and other electrical induced therapies, etc., which use electric currents to go deeper past the stratum corneum to stimulate cells underneath the skin may be employed in the device. The combination of the electrical induced therapies and microdermabrasion create aqueous pathways to increase the permeability of the drugs and/or fluids which are delivered from a supply and return reservoir by a vacuum system within the device. A pressure mechanism may also be employed as part of the device.

According to one embodiment, a device for treating a skin surface of a patient comprising a handle having a tip at the proximal end of the handle is provided. The tip has one or more electrodes and an abrading end portion which has an abrasive media and one or more apertures for fluid delivery. The device may also have a vacuum and a vacuum entry port located on the tip at the proximal end of the handle, where the vacuum entry port has one or more apertures for evacuating fluid and debris from the surface of the skin. According to another embodiment, the electrodes, abrading end portion and fluid delivery apertures are positioned on the tip of the handle, where each one individually may be on a removable tip or end structure. When the device has a plurality of removable structures, the end structures may also be separately removable and interchangeable.

In a preferred embodiment, the tip of the device has an outer structure having one or more electrodes and an intermediate structure having an abrading end portion, where the abrading end portion has an abrasive media. The tip of the device also has an inner structure which has one or more apertures for fluid delivery. That is to say, the inner structure is located at the center of the tip. The outer structure is located at the periphery of the tip. The intermediate structure is located between the inner structure and the outer structure. The outer structure, intermediate structure, and the inner structure are coaxial with each other and are in a ring shape. Preferably, the outer structure and intermediate structure form an outer ring and intermediate ring respectively at the tip. The outer ring and intermediate ring can be formed in a circular shape or a non-circular shape. Therefore, the abrading end portion forms at the intermediate ring and encircles the fluid delivery. The electrodes are aligned at the outer ring to encircle the abrading end portion at the intermediate ring. Preferably, at least one of the structures is removable, and more preferably, each of the outer structure, intermediate structure, and inner structure are removable, and most preferably, at least one of the structures is disposable.

According to another embodiment, a method for treating a skin surface of a patient is provided. According to the method, first an abrasion device for treating a skin surface of a patient is selected, wherein the abrasion device comprises one or more electrodes, an abrading end portion having an abrasive media, and one or more apertures for fluid delivery. Next, the abrading end portion of the device is placed on the skin surface of the patient. The patient's skin is then treated by applying the abrasive media to the skin surface of the patient, delivering fluid to the skin surface of the patient, and applying an electrical current to the skin surface of the patient. The patient skin is treated with abrasive media, fluid delivery, and current delivery in the order stated above, simultaneously, or another order. Vacuum may then be applied to the skin surface of the patient.

According to another embodiment, a kit for treating a skin surface of a patient is provided. The kit comprises a skin abrading device comprising a tip, wherein the tip has at least one current delivery tip having one or more electrodes, a plurality of abrading tips, wherein each abrading tip has an end portion with an abrasive media, and wherein the plurality of abrading tips are removable from the device and interchangeable, and a fluid delivery tip having one or more apertures for fluid delivery. Preferably, the tip further comprises a vacuum entry port and also preferably, each of the plurality of abrading tips has a grit size, and the grit size varies for each abrading tip.

For a more complete understanding of the present invention with its objectives and distinctive features and advantages, reference is now made to the following brief description of the drawings and the detailed description of the invention.

BRIEF DESCRIPTION OF THE DRAWING(S)

These and other features, aspects and advantages of the present invention will become better understood from the following description, appended claims, and accompanying figures where:

FIG. 1A shows a skin abrading device 100 according to one embodiment of the present invention;

FIG. 1B is partial side cut-away view of the device 100, shown in FIG. 1A, according to the present invention;

Figure 2A:
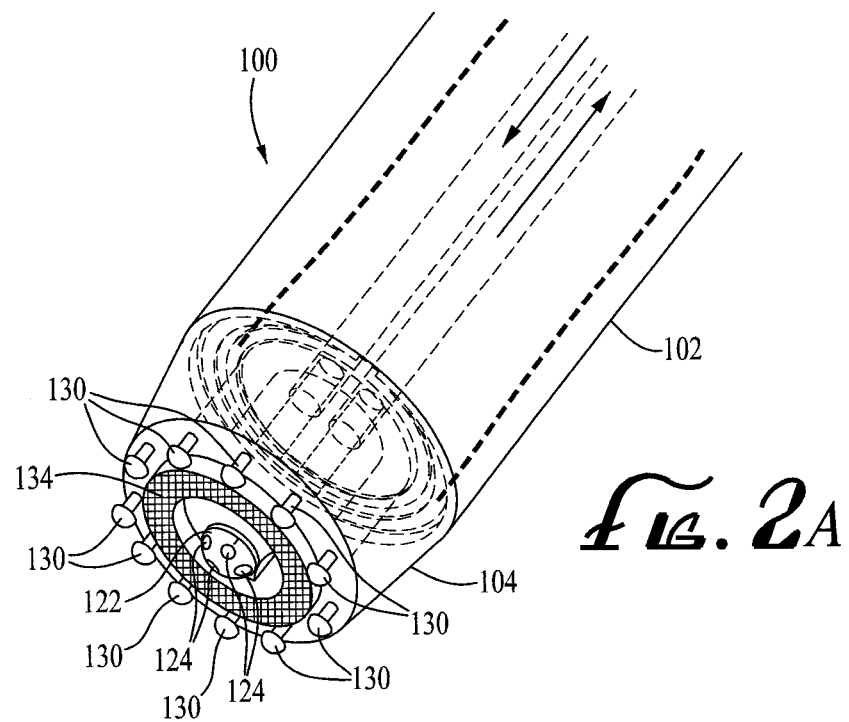
Figure 2B:
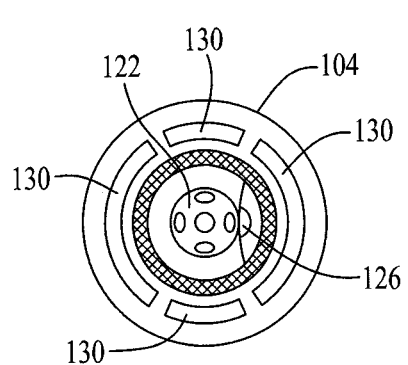
Figure 2C:
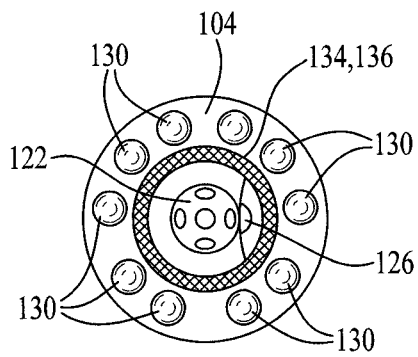
Figure 4:
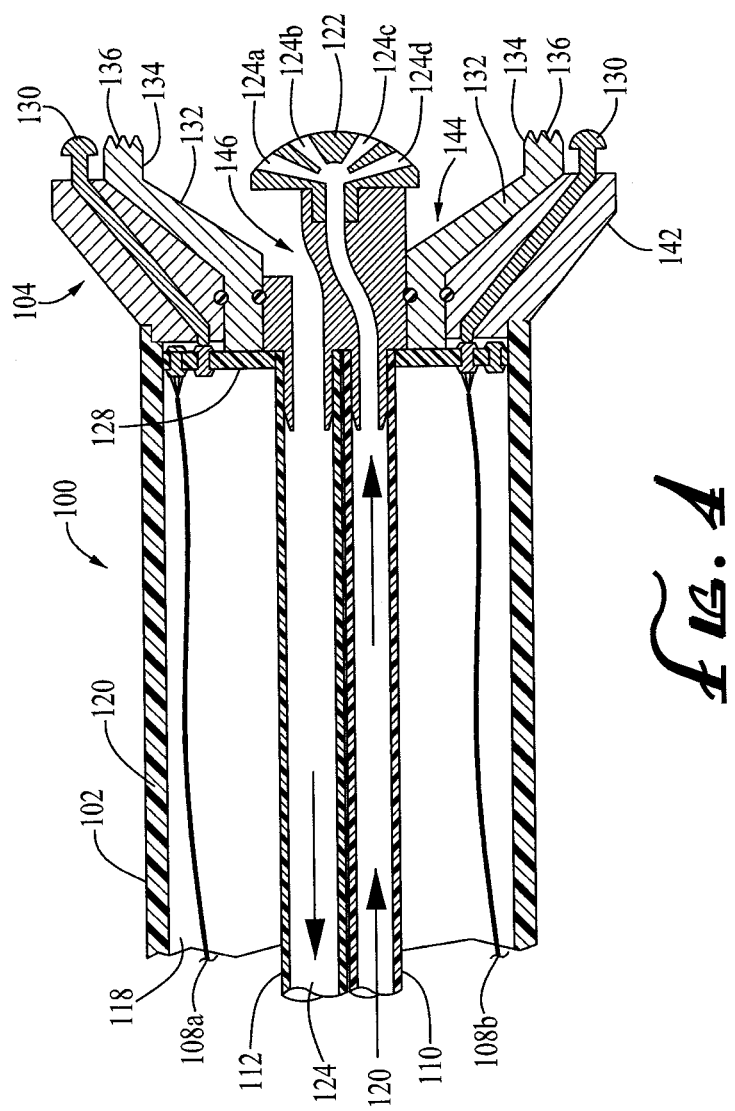

FIG. 2A is a top perspective view of the device 100, shown in FIG. 1A and FIG. 1B, showing the tip 104 of the device 100, according to the present invention;

FIG. 2B and FIG. 2C are alternate embodiments for the tip 104 of the device 100, according to another embodiment of the present invention;

FIG. 3A is a side view of one embodiment of the device 100, having a plurality of removable, exchangeable, and attachable tips according to another embodiment of the present invention;

FIG. 3B is a side view of another embodiment of one of the tips shown in FIG. 3A;

FIG. 4 is a partial side cut-away view of the device 100 having a wide-angle tip 104 according to another embodiment of the present invention;

FIG. 5A is a side view of another embodiment of the device 100, having a plurality of removable, exchangeable, and attachable tips, where the electrodes 108a, 108b, are concentric circles, according to another embodiment of the present invention;

FIG. 5B is a partial side cut-away view of the device 100 shown in FIG. 5A, having electrodes 108a, 108b, which are concentric circles, according to another embodiment of the present invention; and FIG. 6A shows an alternate embodiment of the skin abrading device 100 according to another embodiment of the present invention, having a divided handle 102a and 102b; and FIG. 6B is a cut-away view showing the divided handle 102a and 102b of FIG. 6A.

Figure 7:
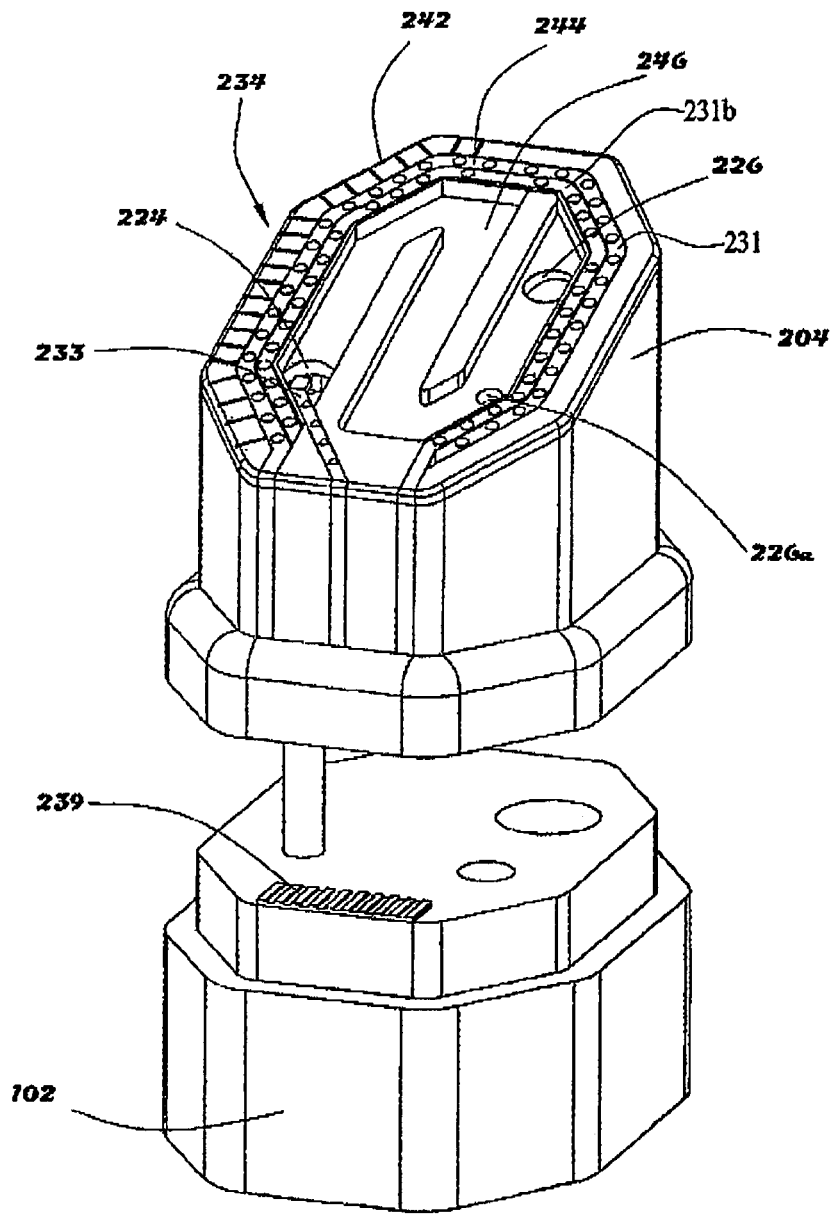
Figure 7A:
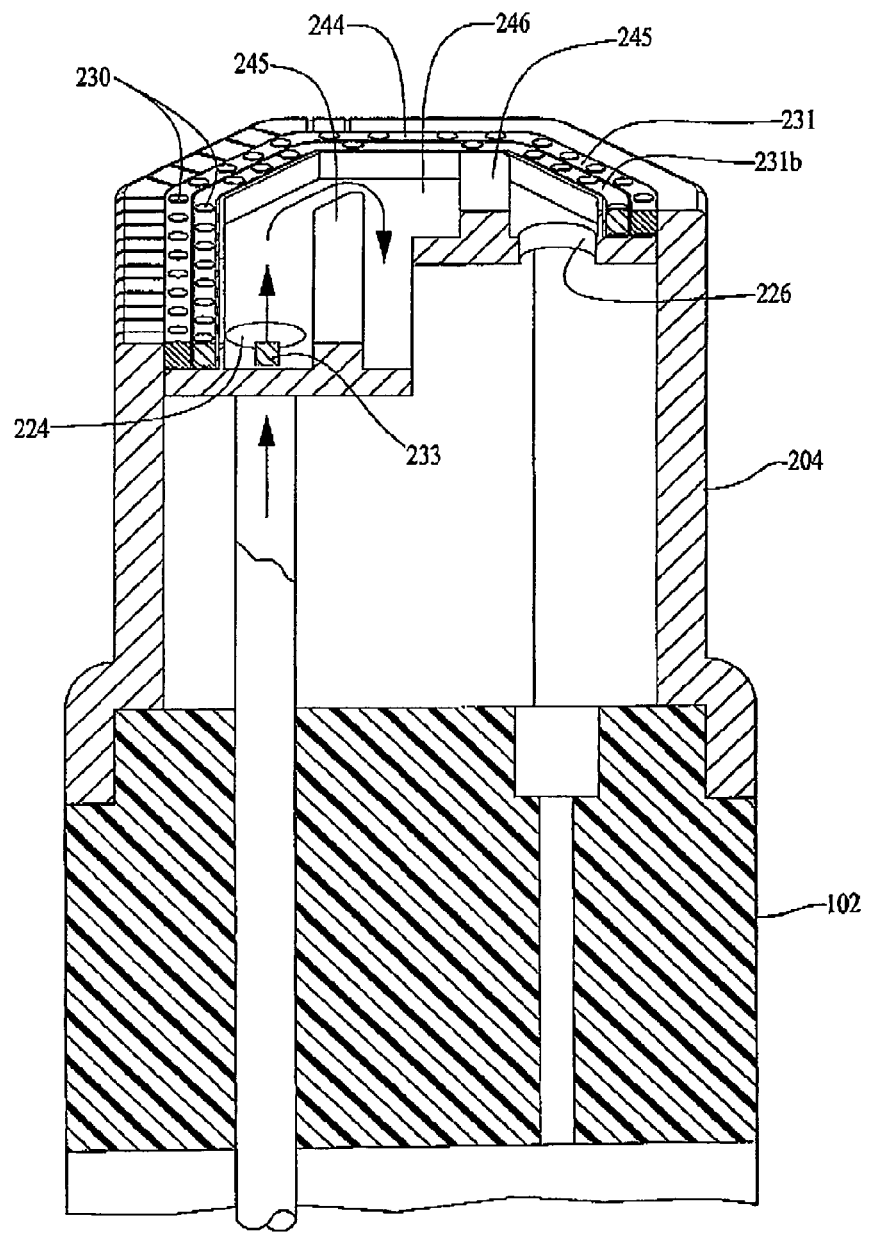

FIG. 7 is a perspective view of the tip detachably coupling at the handle according to another embodiment of the present invention FIG. 7a is a cross sectional view of the tip showing the fluid detouring path to the embodiment of the present invention.

Figure 8:
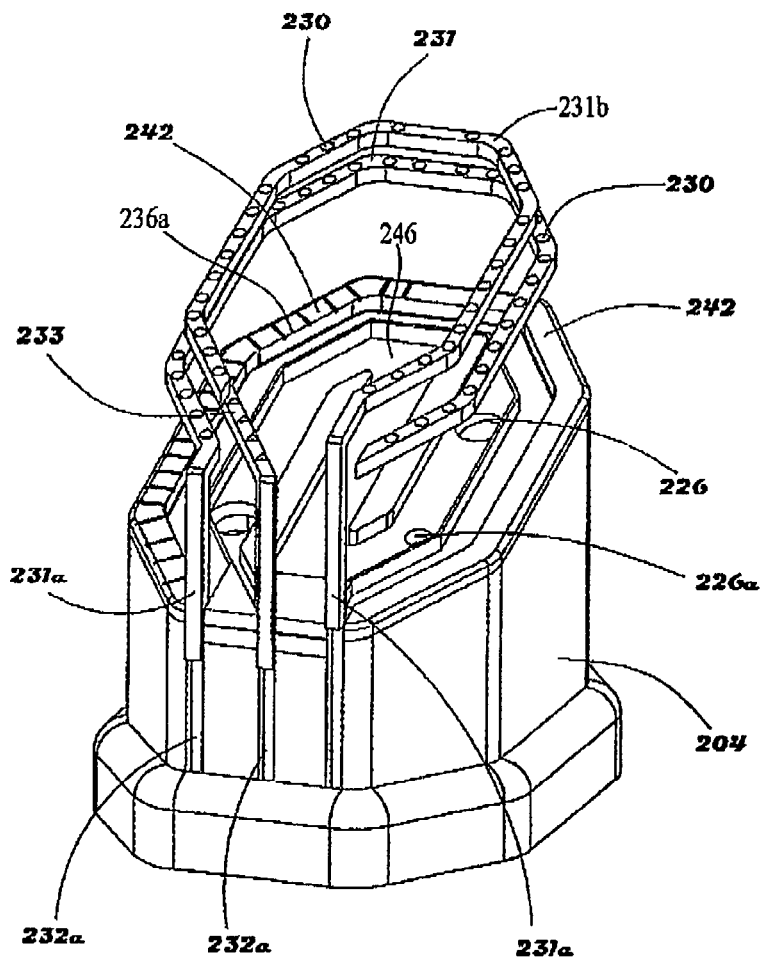

FIG. 8 is an exploded view of the tip according to the above embodiment of the present invention, showing the replacement of the electrode rings.

Figure 9:
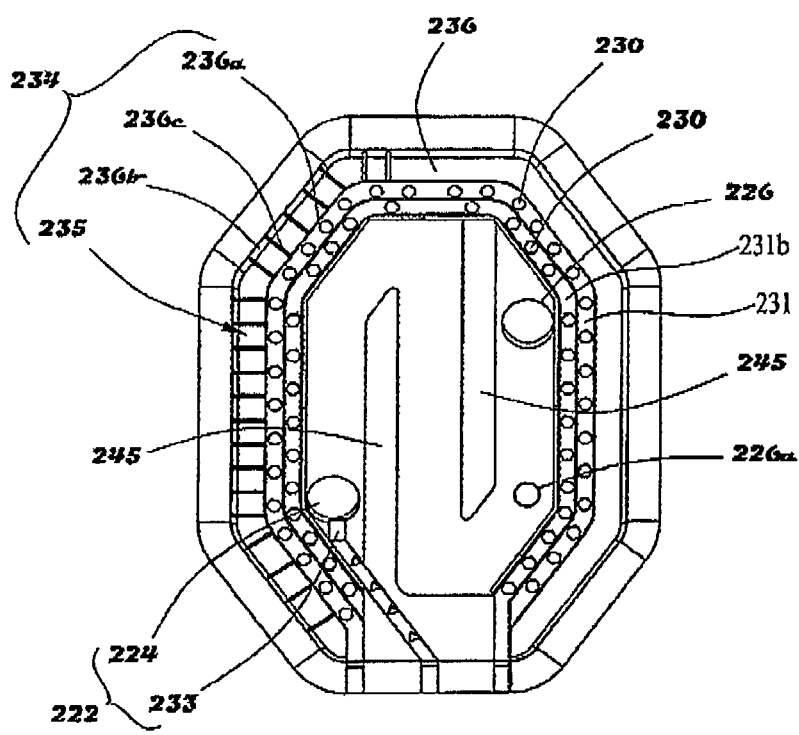

FIG. 9 is a top view of the tip according to the above embodiment of the present invention.

Figure 10:
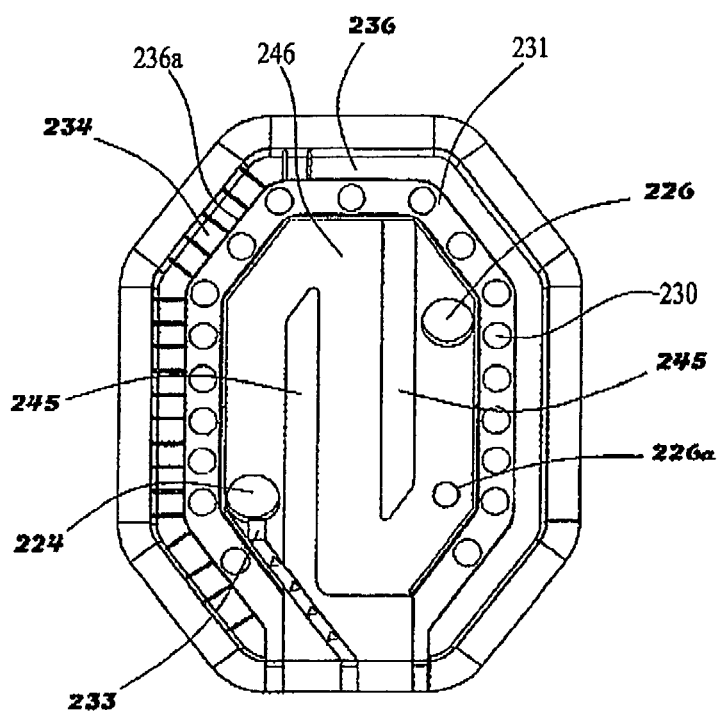

FIG. 10 is a top view of the tip according to the above embodiment of the present invention, showing one electrode ring at the intermediate structure.

Figure 11:
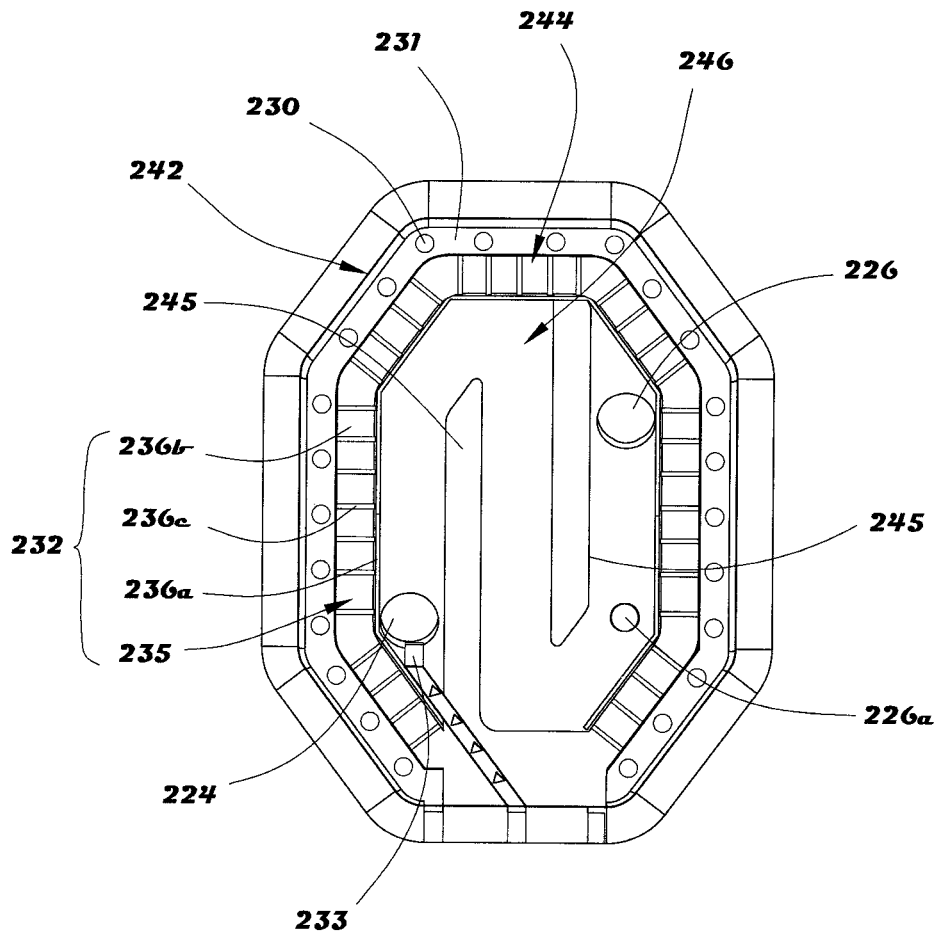

FIG. 11 is a top view of the tip according to the above embodiment of the present invention, showing the alternative of the outer and intermediate structures.

Figure 12:
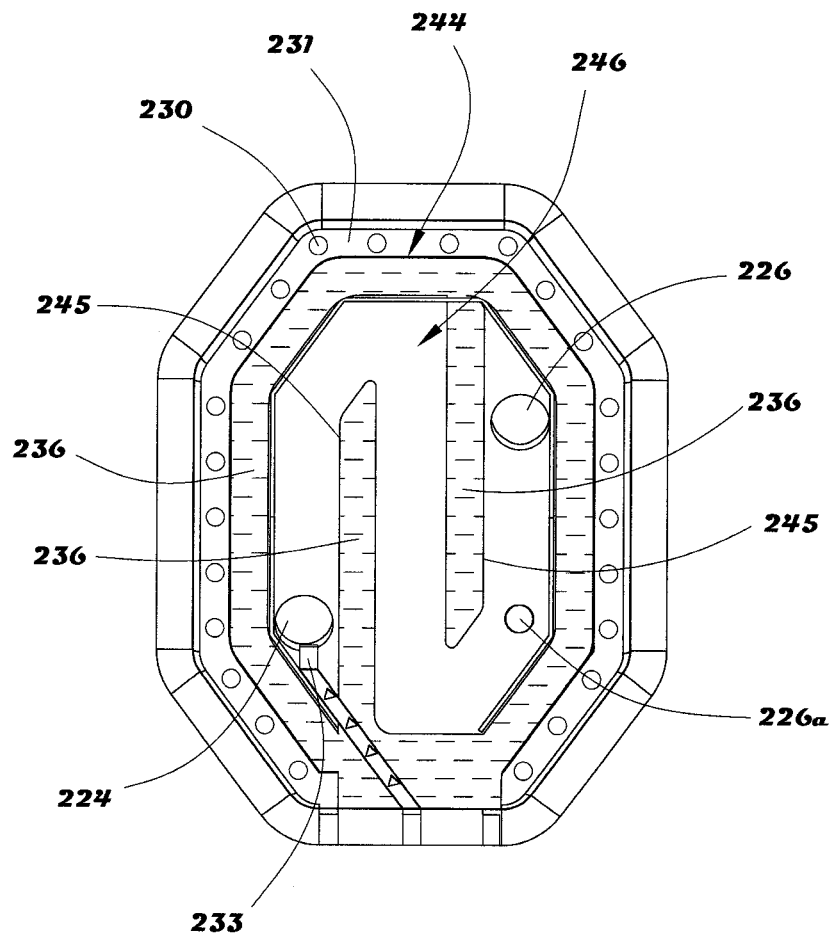

FIG. 12 is a top view of the tip according to the above embodiment of the present invention, showing how to increase the abrading surface of the tip.

Figure 13:
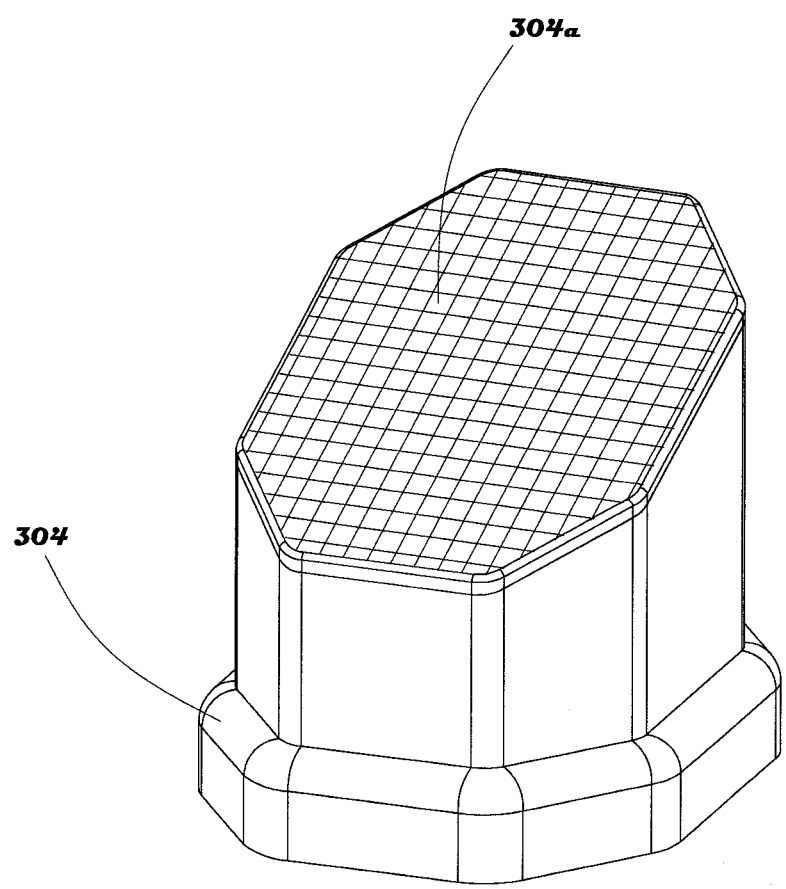

FIG. 13 is a perspective view of the tip detachably coupling at the handle according to another embodiment of the present invention, showing the electrode skin treating tip.

Figure 14:
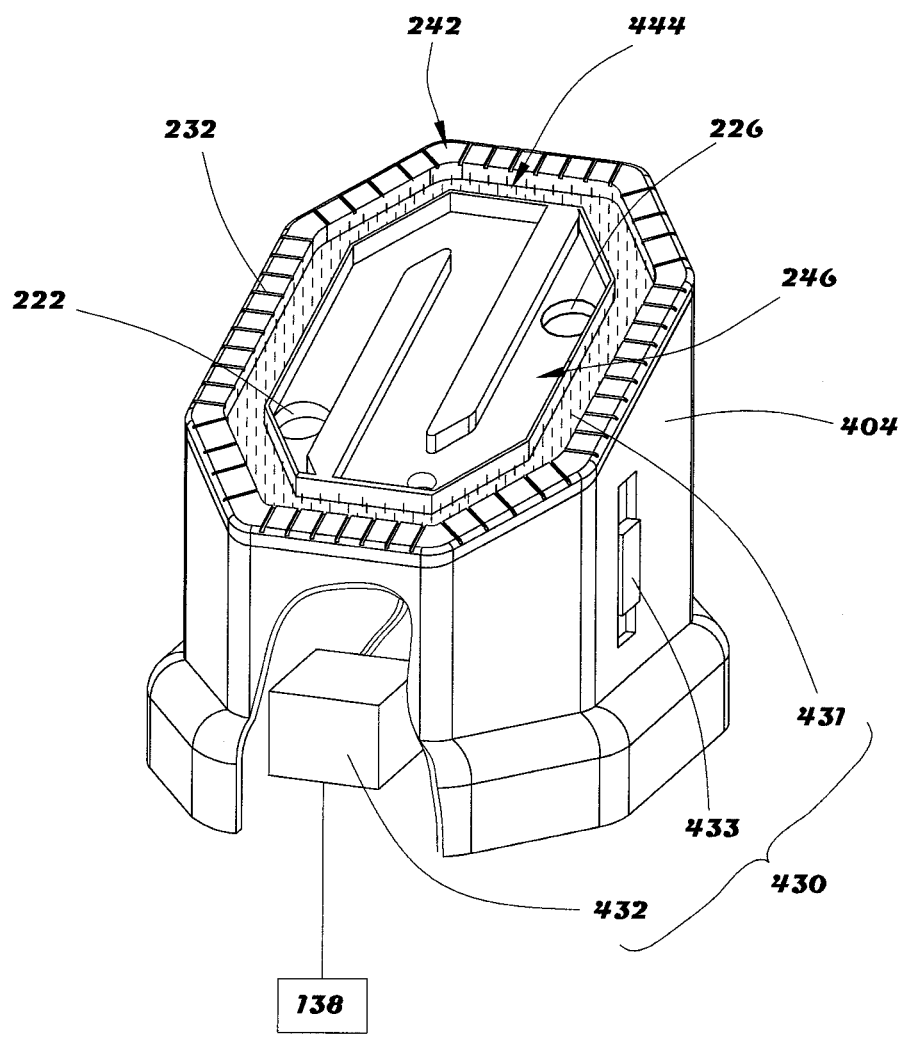

FIG. 14 is a perspective view of the tip detachably coupling at the handle according to another embodiment of the present invention, showing the micro-needle skin treating tip.

Figure 15:
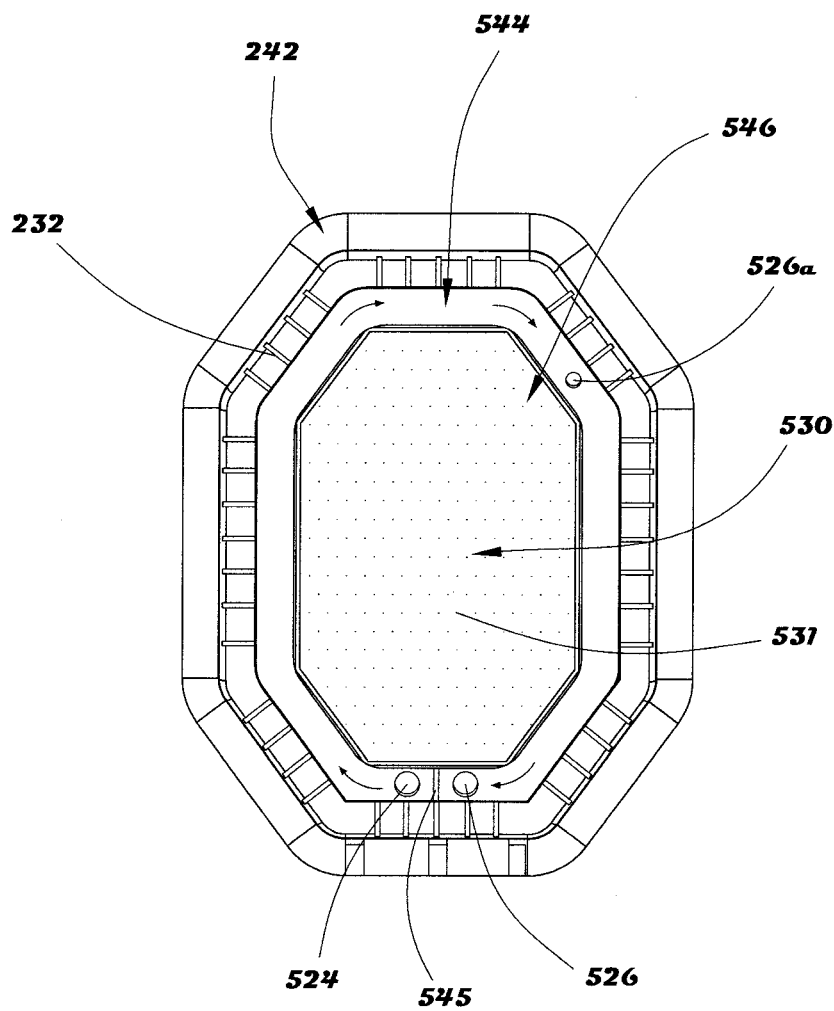

FIG. 15 is a modification of the micro-needle skin treating tip according to the above embodiment of the present invention.

DETAILED DESCRIPTION OF THE INVENTION

According to the present invention, a device, i.e. a microdermabrasion device, for increasing the permeability of the skins surface to fluid and/or drug delivery is described. In general, permeation of drugs and/or fluids through the skin occurs at a slow rate, if at all. The stratum corneum acts as a barrier that limits the penetration of substances through the skin. Application of high-voltage pulses to the skin increases its permeability (electroporation) and enables the delivery of various substances into and through the skin. The application of electroporation to the skin has been shown to increase transdermal drug delivery. Moreover, electroporation, used alone or in combination with other enhancement methods, expands the range of drugs (small to macromolecules, lipophilic or hydrophilic, charged or neutral molecules) that can be delivered transdermally. The efficacy of transport depends on the electrical parameters and the physicochemical properties of drugs. The in application of high-voltage pulses is well tolerated.

According to one embodiment of the invention, a device comprising an abrading surface, fluid delivery, current delivery; and fluid vaccuation is described. The device enhances fluid delivery through the stratum corneum by first delivering an abrasive media to the surface of the skin to prepare the skin for fluid delivery. Next, the device delivers fluid to the surface of the skin, with simultaneous current delivery (electroporation). The combination of skin abrasion, followed by simultaneous fluid delivery with electroporation allows for deep penetration of fluid through the skin by increasing the skin's permeability. In addition to enhancing fluid delivery through the stratum corneum, the device resurfaces the outer surface of the skin, removing dead skin cells and the outer layer of dermis, along with other superficial imperfections. Unlike known microdermabrasion devices, the results achieved with the device of the present invention will have enhanced and longer lasting results, namely, because skin enhancing fluids and drugs are delivered more deeply into the skin with the simultaneous electrooporation, and the electrical induced therapy itself has skin enhancing properties, such as increased collagen production, muscle tone, and overall skin elasticity and firmness.

The device and methods described herein have an efficient fluid supply/return for transdermal/topical delivery of skin enhancing drugs and medicaments. This feature of the invention has been found to be particularly important since presently known technologies use a gel which is applied to the skin which limits the penetration of effective ingredients because of the greater molecular weight of the gel. Macromolecule delivery through a liquid, which can be accomplished with the present invention, is accordingly more effective than prior art technologies which use a gel. The application of an abrasive as described in this invention solves this issue of lowering the impedance of the stratum corneum thus further improving drug delivery to the skin. Accordingly, the device and methods of the present invention, which include fluid delivery with electro-current and a vacuum source, enable simultaneous application of fluids containing skin enhancing drugs, with increased topical delivery through an abrading surface, to achieve the maximum effect. The abrading surface, which is applied to the skin preferably prior to fluid/drug delivery, increases topical drug delivery and penetration of the drug to the lower layers of the skin. These features of the invention are an improvement over prior art technologies which lack a fluid delivery and a vacuum source and more particularly in combination with an abrading surface and electro-current application to accomplish skin resurfacing and enhancement.

As used in this disclosure, the term "comprise" and variations of the term, such as "comprising" and "comprises," are not intended to exclude other additives, components, integers or steps.

In one embodiment, the present invention is a device for enhancing fluid delivery to the skin. Referring now to FIG. 1A, a skin abrading device 100 having fluid and current delivery is shown. The device 100 comprises a handle 102, a tip 104, and a distal end 106. Positioned at the distal end are one or more conduits such as an electrical conduit 108, a fluid delivery conduit 110, and a vacuum conduit 112. The skin abrading device 100 may further include one or more switches for controlling the device 100 such as a switch 114 and/or 116 for controlling electrical current delivered via the electrical conduit 108, and/or control vacuum and/or fluid delivery from the fluid delivery and vacuum conduits 110 and 112. However, in other embodiments, these switches are positioned remotely on an adjunct device. The optional vacuum function of the evacuates fluid and skin debris from the surface of the skin and delivers the evacuated fluid and skin debris to an optional waste container (not shown) which may be positioned on the handle or in an adjunct device.

As shown in FIG. 1A, the handle 102 may be cylindrical with molded hand grip, or it may have other configurations such as cylindrical (without a molded hand grip), or other variations, including elliptical, square, rectangular, and variations thereof. The handle 102 may be formed of various materials as known to those in the art including any suitable plastic, metals, such as aluminum, stainless steel, and other alloys, and combinations of metal and plastic. Preferably, the handle 102 is made from a high density plastic material.

Referring now to FIG. 1B, a partial side cut-away view of the device 100 shown in FIG. 1 is shown. As shown in FIG. 1B, the handle 102 of the device 100 comprises an interior 118 and an outer casing 120. The fluid delivery conduit 110 is positioned in the interior 118 of the handle 102 and delivers fluid 120 from a reservoir (not shown) in an adjunct device through the fluid delivery conduit 110 and out the tip 104 of the device 100. The fluid 120 exits the tip 104 through a fluid delivery tip 122 having one or more apertures 124. Also positioned within the interior 118 of the handle 102 is the vacuum conduit 112 which pulls a vacuum from a vacuum pump (not shown) stationed in an adjunct device through the vacuum conduit 112. The vacuum conduit 12 has a vacuum entry port 126 positioned within the tip 104 for evacuating fluids and other debris from the surface of the skin. The interior 118 of the device 100 has one or more electrical conduits 108a, 108b, which deliver current either to an electronics board 128, which then delivers current to one or more electrodes 130, shown as 130a and 130b. Positioned within the tip 104 is an abrading structure 132 having an abrading end portion 134, which comprises an abrasive media 136. Within either the interior 118 of the device, electronic control circuitry 138 may be positioned for controlling current to the electrodes 130.

Referring now to FIGS. 2A, 2B, and 2C, preferred embodiments of the tip 104 of the device 100 are shown. As shown in FIG. 2A, the tip 104 may be somewhat tapered at the end, or in other embodiments, the tip 104 may be substantially cylindrically shaped or other, such as oval shaped, squared, or rectangularly shaped. As also shown in FIG. 2A, preferably, the fluid delivery tip 122 is domed shaped, having a plurality of apertures 124, such that a spray effect is achieved with the fluid delivery tip 122. (However, in other embodiments, the fluid delivery tip 122 may be flat, and/or have a single aperture 124. Multiple apertures 124 spread the liquid evenly along the area of the skin. Preferably, the fluid delivery tip 122 is positioned with respect to the tip 104, electrodes 130, and abrading structure 132 such that the fluid delivery tip extends slightly beyond or substantially flush with the abrading structure 132.

The tip 122 of the dome creates a planar surface of the skin preventing the vacuum suction from causing a subcutaneous hemotoma which is caused when the lining of blood vessels are damaged and blood escapes through the skin.

The vacuum entry port is positioned with respect to the tip 104, such that the vacuum entry port 126 minimizes skin trauma and ruptured capillaries, veins and arteries from the vacuum 124, yet creates a suitable vacuum to evacuate fluid and debris from the skin's surface. According to a preferred embodiment, the vacuum entry port 126 is positioned on the tip 104 such that when the tip 104 of the device 100 is applied to the surface of the skin, a space is created between the tip 104 and the vacuum entry port 126 to create a vacuum, known in the art as a closed loop system.

In a preferred embodiment, the fluid delivery tip 122 is substantially flush to the skin with respect to the abrading end portion 134 of the abrading structure 132 and the electrodes 130 such that when the device 100 is applied to the skin, the skin stays relatively flat during treatment. According to this embodiment, when the abrasive media 136, vacuum 124, fluid 120, and electric current 140 are applied to the skin with the configuration described with respect to this embodiment, having the various structures of the tip 104 substantially flush to the skin minimizes the possibility of skin trauma associated with the pulling up of skin in a space of vacuum 124.

In an alternate embodiment, the vacuum entry port 126 can be positioned in other portions of the tip 104 to provide an optimal vacuum of concurrent liquid delivery and/or removal of skin debris. However, the vacuum entry port 126 is preferably positioned to keep a higher level of fluid within the tip of the handle during treatment so as to have a higher absorption and penetration rate of ingredients contained in the fluid, into the skin, while still evacuating skin debris and preventing the fluid 120 from flowing away from the desired treatment area and/or falling off the skin.

The abrading structure 132 is positioned with respect to the tip 104, such that the abrading end portion 134 of the abrading structure 132 is substantially flush to the surface of the skin. In other embodiments, the abrading structure 132 may be lowered or raised with respect to the end of the tip 104 to provide skin contact, as desired by the user.

In a preferred embodiment, the abrading structure 132 has a range of abrasiveness on the abrasive media 136 from a substantially smooth surface (no abrasion) to very abrasive depending on the treatment type. As shown in FIGS. 1B, and 2A-2B, the abrading structure 132 is positioned on the outer edge of both a fluid supply, i.e., the fluid delivery tip 122 and vacuum port 126 and on the inside of the electrodes 130. However, according to the present invention, other arrangements of the abrading structure 132, electrodes 130, and fluid delivery tip 122 and vacuum port 126 are possible, as will be understood by those of skill in the art.

The abrading structure 132 may be reusable or disposable, in part or entirely. For example, according to one embodiment, the abrading end portion 134 and the abrasive media 136 are integral to the abrading structure 132. According to this embodiment, the abrading structure may be reusable or disposable in part or entirely. When the abrading structure 132 is reusable, it is preferably designed to be sanitized and cleaned between uses and reused. In an alternate embodiment, the abrasive media 136 is positioned on the abrading end portion 134 in a removable fashion, such as a removable strip. According to this embodiment, the abrading structure 132 is generally reusable and the abrasive media 136 on the abrading end portion 134 is preferably disposable.

The abrasive media 136 comprises a material suitable to abrade the surface of the skin such as sand paper, rough textiles (such as dermal grade fabrics that are used in cosmetic microdermabrasion, typically made from 100% medical grade nylon and have a plurality of coatings and finishes), wire brushes, carbon fibers, and microneedles. The material can be conductive or non-conductive. According to one embodiment, the abrasive media 136 comprises a non-conductive sand paper. In one embodiment, the sand paper is white aluminum oxide, a non-conductive material, readily available at low cost in medical grade. This material is able to withstand elevated temperatures, such as those typically present in any vitrification process that may be necessary for high volume binding/fabrication to produce the abrasive tip. According to other embodiments, a material softer than aluminum oxide is preferred so that the material is less irritating to the skin than aluminum oxide. According to this embodiment, the abrading media 136 comprises polymeric beads. Generally, polymeric beads provide a softer, less irritating material than aluminum oxide. However, other materials according to the invention may be used as the abrading media 136, where the material is selected based on the particular individual to be treated and the purpose of the treatment. Accordingly, for different individuals, different materials may be substituted for the above-listed materials. In other embodiments, the abrasive media 136 comprises a conductive material. Suitable conductive materials include, but are not limited to, metals, carbon, conductive polymers and conductive elastomers.

The abrading end portion 134 may have a variety of suitable thicknesses and diameters. According to one embodiment, abrasive particles are coated onto the abrading end portion of the abrading structure 132. In some embodiments, the abrading structure 132 and abrading end portion 134 comprise a unitary plastic structure, such as acrylonitrile butadiene styrene (ABS). According to this embodiment, the abrasive media is an abrasive coating adhered to the abrading end portion 132, or the abrasive media 136 is of a unitary construction with the abrading structure 132 and abrading end portion 134. According to one embodiment, the abrasive media comprises abrasive particles which are adhered to the abrading end portion 134, where the thickness of the abrasive media 136 is defined by the grit size of the abrasive particles. According to this embodiment, the abrasive particles are generally of a size ranging from about 300 to 50 grit (about 50 to 300 microns), and typically about 100 to 120 grit and may comprise carborundum (aluminum oxide), sodium bicarbonate, polymeric particles, and the like. Coarser particles (at the lower ends of the grit ranges (about 35 to 50, and typically less than 100) may also be provided for use in initial treatments, or treatments on coarser areas of the skin (such as arms), while finer particles (at the higher ends of the grit ranges about 300 and above) may be employed for subsequent treatments. Alternately, the abrading end portion 134 may be formed by knurling, machining, laser treatment or otherwise mechanically or chemically treating the end of the abrading end portion 134 to provide an integral abrasive media 136 which has a unitary construction with the abrading end portion and abrading end structure 132. In a preferred embodiment, the abrasive media 136 is abrasive particles having a grit size of about 120 or lower (approximately 0.0044 inches in diameter).

Typically the abrading end portion 134 will have a thickness ranging from 0.5 microns to 150 microns, preferably ranging from 15 microns to 120 microns. The diameter of the abrading end portion 134 is variable depending on the type of application. For example, in applications having a small area to be permeabilized, the abrading end portion 134 can have a diameter of up to several micrometers, such as from 1 to 25 microns. For applications having a larger area to be permeabilized, the abrading end portion 134 can have a diameter of up to several inches, such as from 0.1 to 5 inches (2.5 mm to 127 mm).

According to the present invention, a current 140 (not shown) is delivered from the device 100 to the surface of the skin through one or more electrodes 130. The electrodes 130 can be a single electrode, or a plurality of nodes or combination thereof, and may further have a variety of configurations and dimensions, such as nodes, bars, etc., as will be understood by those of skill in the art.

Electrical currents, known for application to the skin, which may be used according to the present invention include:

a. Electroporation. Electroporation refers to the application of electric pulses to increase the permeability of cell membranes. According to the present invention, electric pulses are applied to skin cells to increase membrane permeability.

b. Microcurrent. Microcurrent refers to the application of a small current used in a noninvasive electrotherapy technique where electrodes are applied at acupuncture points. In general, 10-500 microamps (Ua) are applied to the surface of the skin and for optimal effectiveness, the current applied to the skin should not cause an actual "visual" contraction of the facial muscles. In some applications, electroporation refers to the process of applying a microcurrent to the surface of the skin.

c. Iontophoresis. Iontophoresis refers to a therapeutic type of transcutaneous drug delivery in which electric current is applied to the skin to enhance absorption of large polar or hydrophilic molecules and peptides—e.g., insulin, and control therapeutic delivery. According to the present invention, a galvanic current is applied an ionizable agent in contact with a surface of the skin, by means of an appropriate electrode, to hasten the movement into the tissue of the ion of opposite charge to that of the electrode. Accordingly, skin enhancing agents which are polar or hydrophilic may be delivered into the skin.

d. Sonophoresis. Sonophoresis refers to a process that exponentially increases the absorption of semisolid topical compounds (transdermal delivery) into the epidermis, dermis and skin appendages. Sonophoresis occurs where ultrasound waves stimulate micro-vibrations within the skin epidermis and increase the overall kinetic energy of molecules making up topical agents. Skin enhancing agents may be mixed with a coupling agent (gel, cream, ointment) to transfer ultrasonic energy from the ultrasound transducer (i.e., electrode) to the skin and enhancing drug transport through the skin.

e. Galvanic. Galvanic or Galvanic current refers to the current which is the electrical current used in the process of Iontophoresis.

f. Ultrasound. Ultrasound or ultrasonic current refers to the current used in Sonophoresis. Ultrasound is cyclic sound pressure with a frequency greater than the upper limit of human hearing. Although this limit varies from person to person, it is approximately 20 kilohertz (20,000 hertz) in healthy, young adults and thus, 20 kHz serves as a useful lower limit in describing the ultrasonic current applied via the electrodes in the present invention.

g. Ultrasonic Cavitation. Ultrasonic Cavitation refers to an advanced ultrasonic machine having 3 MHz and 1 MHz ultrasound frequencies for the body and a 1.4 MHz ultrasonic frequency for the face, and an ultrasonic cavitation wavelength at 47 KHz. In Ultrasonic Cavitation, the ultrasonic waves are able to act on the skin surface (3 MHZ ultrasound), providing skin tightening as well in the deep layers, (cavitation) providing real results, after the treatment, in terms of cellulite and localized adiposity. It has been shown to be able to eliminate centimeters of belly, buttocks, hips and thighs without any side effects. Ultrasonic waves in a specific range from 20 to 70 KHz are able to cause the "cavitation" effect: focused high energy waves which creates micro bubbles of vapor inside the adiposities and in the interstitial liquids of cellulite.

h. Acoustic Cavitation. Acoustic Cavitation refers to a non-flowing system where the ambient pressure can be varied by sending sound waves through a liquid. The ultrasonic sound waves are made up of alternate compressions and rarefactions. During the rarefaction cycle (low pressure) a lot of microscopic bubbles will grow and during the compression cycle (high pressure) each bubbles undergoes a collapse or implosion.

i. Mesotherapy. Mesotherapy refers to a procedure in which multiple tiny injections of pharmaceuticals, vitamins, etc., are delivered into the mesodermal layer of tissue under the skin, to promote the loss of fat or cellulite.

J. Radio Frequency. Refers to a procedure using a beam of radio frequency energy to target deeper layers of the skin by heating them up. This creates stimulation of the skin and in particular, the collagen, a substance which gives elasticity to the skin. The radio frequencies cause water molecules in the deeper layers of skin to vibrate. This in turn creates friction which causes the heating effect. When heat is applied to collagen fibres, they shrink and tighten up, and over time following the treatment, new collagen also forms.

k. Hot and cold therapies. Refers to using an electrical current and other modalities to create different adjustable temperatures ranging from hot (up to 140 degrees Fahrenheit) to cold (down to 5 degrees Fahrenheit) to treat the surface layer skin by softening and/or tightening collagen fibers.

In a preferred embodiment of the present invention, a microcurrent is applied to the skin, i.e., electroporation. According to this embodiment, the current of the device 100 is set for a wave form with power between 10-500 microamps (Ua). The current 140 (not shown) is delivered through the device 100 and through one or more electrodes 130 to the surface of the skin. Treatment can be substantially stationary in certain areas, or vary in the degree of motion, up to sweeping lines.

According to another embodiment, a combination of two or more frequencies of current are applied from the device 100 to a patient. Accordingly, in some embodiments the device is capable of delivering a plurality of different frequencies (i.e., types) of current, either individual applied or concurrent. For example, an ultrasonic current may be applied from the device 100 to a patient, followed by delivery of a microcurrent from the device 100 to the same patient. The treatment may be in one treatment area, or over a plurality of treatment areas, such the delivery of microcurrent to the face, followed by delivery of ultrasonic current to the arms. The plurality of frequencies may be used on one patient for application of different electric currents. For example, ultrasound and microcurrent have different ways of penetrating fluids and treating the skin. The concurrent combination of these and other electric modalities shown in device 100 is to provide a more effective treatment.

Referring again to FIG. 1B, fluid 120 is delivered from a fluid reservoir (not shown), which may be either part of the handle or in a separate reservoir, such as a plastic or glass tube serum, through the fluid delivery conduit 108 and out the fluid delivery tip 122 in the tip 104 of the device 100. Fluid delivery may be used in the device for cleaning of the skin, as a vehicle for delivery of a therapeutic agent, or it may be the therapeutic agent itself, and/or the fluid may be an ionic agent to facilitate delivery of current 140 through the electrodes 130. The fluid may include one or a plurality of suitable skin enhancing agents, and/or conductive ingredients, or other suitable agents for skin cleaning and skin enhancement or facilitation of current delivery, such as water, salts, ionic or non-ionic surfactants, preservatives, alcohol, glycerol, gel, and other similar agents. Various mixtures of these agents may be formulated into fluids with various conductivity levels, depending on the desired application. Preferably, at least one of the fluids used in a method according to the present invention is a "highly conductive fluid" or a "fluid with a high conductivity" meaning a fluid with a conductivity from about 1,000 to about 100,000 (µSiemens/cm) to facilitate current delivery. Other fluids, such as a "fluid with a low conductivity", meaning a fluid with a conductivity from about 0.1 to about 999 (µSiemens/cm), are used according to the invention in other applications, such as cleaning, and/or delivery of a skin enhancing or therapeutic agent. A highly conductive fluid is used according to the present invention to provide a conductive path through the skin. In a preferred embodiment, at least one fluid with a conductivity of at least 500 to about 50,000 uSiemens/cm is used.

Therapeutic or skin enhancing fluids useful in the device 100 according to the present invention may be of a variety of therapeutic agents. For example, the fluid may be a skin treatment liquid, a lotion liquid, and/or a vitamin liquid, or a combination thereof. The fluid may also be a pharmacologically-active agent, where the fluid carries a chemical agent of a suitable concentration. Examples of such agents include TCA (trichloroacetic acid), a glycolic acid including an alphahydroxy acid (AHA), a lactic acid, a citric acid, and phenol, one or in combination with other agents or fluids. Examples of other therapeutic or skin enhancing agents include type A botulinum toxine, phosphatidylcoline, aminophylline, hyaluronic acid, L-carnitine, vitamins, amino acids, collagen, lidocaine, heparin, elastine, compounds for Mesotherapy procedures, glutathione, hormone replacement agents, hyaluronidase, MTE-4 (Copper-Manganese-Zinc Sulphate-Chromium), ionic skin tissue growth gels, enzymes, peptides and steroids.

Other ingredients can include plant and fruit derived ingredients, such as enzymes and stem cells derived from fruits and/or plants, etc. Since microdermabrasion is a controlled injury of the skin by abrading the surface layer to cause a wound healing response, other known healing and anti-inflammatory ingredients such as cortisone, aloe extract, etc.

may be used to increase healing response time and also act as an anti-fungal, anti-viral, anti-bacterial and acaricidal activity against skin infections such as acne, etc. may be used individually or in any combination with other sterile fluids, drugs, and other skin enhancing and/or therapeutic agents.

Other agents and preferred viscosity parameters may be found in "Advanced drug delivery reviews", 56 (2004) 659-674.

Referring again to FIG. 1B, a vacuum 124 may be applied to the surface of the skin from a vacuum pump (not shown) through the vacuum conduit 112 and vacuum entry port 126 on the tip 104 of the device. Preferably, the vacuum pump which supplies the vacuum 124 to the device 100 has a rating of 2.9 A, with a max flow rate of 2 cu.ft/min, a power rating of 120 W, with a 60 Hz frequency, and preferably RoHS compliant, although other embodiments are possible. In general, the vacuum 124, used during a treatment and applied to the surface (or just above) the skin of a patient, is a continuous flow and preferably can be adjusted with a flow control valve to increase or decrease vacuum pressure.

Referring now to FIG. 3A, a skin abrading device 100, having a plurality of removable, exchangeable, and attachable tips, according to a preferred embodiment of the invention is shown. As shown in FIG. 3A, the tip 104 of the device 100 comprises multiple nesting (e.g., interconnected) structures which are removable/attachable from the handle 102. The outer structure 142 of the tip 104 comprises the electrodes 130 at the proximal end of the tip 104 and wiring (not shown) for delivering current 140 (not shown) to the electrodes 130. Positioned within the outer structure 142, is the intermediate structure 144, which is also the abrading structure 132. The inner structure 146 comprises the fluid delivery tip 122 and vacuum entry port 126. When the structures 142, 144, and 146 (i.e., tips) are assembled, the tip 104 of the device 100 will have the configuration shown in FIGS. 1A, 1B, and 2A-2C.

That is to say, the inner structure 146 is located at the center of the tip. The outer structure 142 is located at the periphery of the tip. The intermediate structure 144 is located between the inner structure 146 and the outer structure 142. The outer structure 142, intermediate structure 144, and the inner structure 146 are coaxial with each other and are in a ring shape. Preferably, the outer structure 142 and intermediate structure 144 form an outer ring and intermediate ring respectively at the tip. The outer ring and intermediate ring can be formed in a circular shape or a non-circular shape. Therefore, the abrading end portion forms at the intermediate ring and encircles the fluid delivery tip 122 and vacuum entry port 126 of the fluid delivery. The electrodes 130 are aligned at the outer ring to encircle the abrading end portion at the intermediate ring.

The outer structure 142, intermediate structure 144 and inner structure 146 are connected to the handle 102 with a suitable connection, such as compression fitting, threaded fittings, etc. In a preferred embodiment, one or more of the outer structure 142, intermediate structure 144, and inner structure comprise stainless steel. In one preferred embodiment, the intermediate structure 144 comprises a reusable stainless steel abrading structure 132 having an abrading end portion 134 which has a diamond coated abrasive as the abrasive media 136. In another preferred embodiment, the intermediate structure 144 comprises a disposable (preferably translucent) plastic abrading structure 132 having a disposable abrasive media 136 positioned on the abrading end portion 134. In another preferred embodiment, the inner structure, comprising the fluid delivery tip 122 and the vacuum entry port 126, are one or more of transparent, detachable, and/or disposable. Although the outer structure 142, intermediate structure 144, and inner structure 146 have been described herein as removable, exchangeable, and attachable, it will be understood by those of skill in the art that one or more of the outer structure 142, intermediate structure 144, and inner structure 146 may be affixed to the handle 102 in a permanent, or not-easily removable fashion. However, in other embodiments, one or all of the structures 142-144 may be one piece in any arrangement or separate individual connections. For example, the device may comprise a handle 102 with an electric current node (i.e., electrode 130) in the middle surrounded by a fluid delivery piece 122 and an abrasive structure 132 making the outer edge of the handle. This is just an opposite arrangement from the arrangement shown in FIG. 3A, and as it will be understood by those of skill in the art, interrelationship of the various tips shown in the Figures is by way of example and other configurations are within the scope of the invention.

Referring now to FIG. 3B, another embodiment of the abrading structure 132 is shown. According to this embodiment, the abrading end portion 134 of the abrading structure 132 comprises one or more grooves 135. The grooves 135 may be differently shaped, such as rounded grooves, or slotted squares. The grooves 135 are provided to abrade the skin more effectively by stretching it, and to better guide skin debris into the vacuum. Preferably, to keep the vacuum 124 sealed, the grooves 135 are substantially even with the edge such that when the abrading structure 132 is applied to the skin, air does not escape. The grooves 135 may have a variety of thickness or radius, shape or design, for different skin types and applications, as will be understood by those of skill in the art. According to this embodiment, extraction can be realized by pressing the abrading end portion 134 and grooves 135 to the skin, such that the grooves 135 act as a comedone extractor on a pore. For example, when the abrading end portion 134 having grooves 135 is pressed to the skin, oil and sebum will be released from the pores.

Referring now to FIG. 4, a partial side cut-away view of the device 100 having a wide-angle tip 104 is shown. As shown in FIG. 4, the same numbers refer to the same features shown in FIG. 1B, with the differences noted below. According to this embodiment, the tip 104 of the device is a wide angle tip, where the fluid 120 exits the tip 104 through a fluid delivery tip 122 having a plurality of apertures 124a-124d. According to this embodiment, the wide angle tip allows for an increased area for fluid delivery and more apertures for fluid delivery. The interior 118 of the device 100 has one or more electrical conduits 108a, 108b, which deliver current either to an electronics board 128, which then delivers current to one or more electrodes 130, or directly to the electrodes. As the tip 104 is a wide-angle tip, the electrodes are positioned further from the center of the tip 104 and in some embodiments, this allows for additional or wider electrodes 130 than the tapered tip 104 shown in FIG. 1A and FIG. 1B. Positioned within the wide angle tip 104 is an abrading structure 132 having an abrading end portion 134, which comprises an abrasive media 136. Similarly to the electrodes 108, the abrading end portion 124 and abrading media 132 are positioned further from the center of the device than the tapered tip 104 shown in FIG. 1A and FIG. 1B. This embodiment may be used on a treatment area with a larger surface area that can accommodate the larger tip surface area. The various tips comprising the outer structure 142, intermediate structure 144, and inner structure 146, shown in FIG. 4, may be removable, exchangeable, and attachable, and may be exchanged with other interchangeable tips 142-144, of other dimensions, as described herein.

Referring now to FIG. 5A, a skin abrading device 100, having a plurality of removable, exchangeable, and attachable tips, according to another preferred embodiment of the invention is shown. Unless otherwise noted below, the same reference numbers refer to the same elements as described with reference to FIG. 3. As shown in FIG. 5A, the tip 104 of the device 100 comprises multiple nesting (e.g., interconnected) structures which are removable/attachable from the handle 102. As shown in FIG. 5A, the electrodes 130a and 130b, are concentric circles positioned within the outer structure 144 of the tip 104. Positioned within the outer structure 144, is the intermediate structure 144, which is also the abrading structure 132. The inner structure 146 comprises the fluid delivery tip 122 and vacuum entry port 126. Referring now to FIG. 5B, a partial side cut-away view of the device 100 shown in FIG. 5A, having electrodes 108a, 108b, which are concentric circles is shown. When the structures 142, 144, and 146 (i.e., tips) are assembled, the tip 104 of the device 100 will have the configuration shown in FIG. 5B. The outer structure 142, intermediate structure 144 and inner structure 146 are connected to the handle 102 with a suitable connection, such as compression fitting, threaded fittings, etc. As shown in FIGS. 5A and 5B, the tip 104 is substantially linear with respect to the handle. However, in other embodiments, the tip 104 may be tapered as shown in FIG. 1A or wide-angled, as shown in FIG. 4. The structures 142-146 may comprise any suitable metal such as stainless steel, or may be any suitable plastic that is transparent, detachable, and/or disposable, and may be removable, etc. as shown in FIG. 5A, or substantially fixed, as described herein with respect to other embodiments, as will be understood by those of skill in the art.

Although the electrodes 130, shown in FIG. 5A and other Figures, are shown as positioned on the outer structure 144, the electrodes 130 may be positioned on the inner structure 146 and the fluid delivery portion 122 and/or the abrasive portion 132 may be positioned in the outer and intermediate structures 142 and 144, in a variety of combinations, either removable/attachable or permanently part of the handle, as will be understood by those of skill in the art.)

FIG. 6A shows an alternate embodiment of the skin abrading device 100 according to another embodiment of the present invention. As shown in FIG. 6A, the device 100 has a divided handle 102a and 102b. FIG. 6B is a cross sectional view showing the divided handle 102a and 102b of FIG. 6A. As shown in FIG. 6B, the top portion of the handle 102a comprises the fluid delivery conduit 110 and the vacuum conduit 112 and the bottom portion of the handle 102b comprises the electrical conduits 108a. The tip 104 of the device 100 shown in FIG. 6B, may have one or all of the configurations disclosed herein, including removable/interchangeable outer, intermediate and inner structures 142, 144 and 146 for the tip 104 portion of the device 100, as shown in FIGS. 3-5.

As shown in FIGS. 1-6, each of the embodiments described comprises tip 104 having electrodes 130, an abrading structure 132, and fluid delivery 122. However in other embodiments, the device may have only two of these features, such as the combination of electrodes 130 and fluid delivery 122, without the electrode 130 feature, as will be understood by those of skill in the art.

According to another embodiment, a method for treating a skin surface of a patient is provided. According to the method, a device according to the invention is employed to abrade the skin surface of a patient; deliver fluid to the surface of the skin; and apply current to the surface of the skin. These steps may be performed in the sequence described herein, or the sequence may be altered, depending on the type of procedures to be performed on the patient, as will be understood by those of skill in the art.

In a preferred embodiment, first the abrading end portion 134 of the abrading structure 132 of the device 100 is applied to the skin surface of a patient. Vacuum may optionally be applied to the skin surface to remove any residual debris, such as abrasive media and excess skin, either after or during the abrading portion of the treatment. Then, the skin surface is contacted with the abrading end portion 134 and abrasive media 136 of the device and the abrading end portion 134 of the device 100 is moved over the surface of the skin. Treatment can be substantially stationary in certain areas, or vary in the degree of motion, up to sweeping lines. Next, a fluid is provided to the skin surface through the fluid delivery tip 122 of the device 100. Then, a current 140 is applied to the surface of the skin by transferring current from the electrodes 130 to the skin surface. The current 140 may be applied either to wet or dry skin.

Although the method is described above as being performed in a sequential manner, this is provided by way of example, and is only one of the possible protocols for the method of the invention. Accordingly, according to the method of the invention the various treatments, including skin abrasion, fluid delivery, and/or current delivery may be performed concurrently, or one at a time, in any order, depending on the patient needs and treatment given to any particular patient.

Another embodiment in FIGS. 7 to 9 illustrates a modification of the tip 204 that detachably couples to the handle 102. The tip 204 is a multi-functional tip to provide multiple functions. The tip 204 has a slanted skin applying surface, wherein the outer structure 242, intermediate structure 244, and the inner structure 246 are coaxial with each other and are formed at the slanted skin applying surface with respect to the handle 102. The skin applying surface is a flat surface.

The outer structure 242 of the tip 204 comprises an abrading structure 232, wherein the abrading end portion 234 of the abrading structure 232 comprises one or more abrading edges 236a, 236b. The abrading structure forms an abrasive crown. In FIG. 9, the abrading structure 232 comprises an inner abrading edge 236a and an outer abrading edge 236b, wherein the inner abrading edge 236a and outer abrading edge 236b form in a ring shape, which can be a non-circular ring shape or a circular ring shape. The abrading end portion 234 of the abrading structure 232 comprises a plurality of connecting abrading edges 236c spaced apart with each other and extended between the inner abrading edge 236a and outer abrading edge 236b to form a crown shaped abrading structure. A plurality of grooves 235 are formed between every two of the connecting abrading edges 236c. The grooves 235 may be differently shaped, such as rounded grooves, or slotted squares. The grooves 235 are provided to abrade the skin more effectively by stretching it, and to better guide skin debris into the vacuum. The abrasive media 236 can also be replaced with new abrasive media and placed at the abrading end portion 234 of the abrading structure 232 between the inner abrading edge 236a and outer abrading edge 236b.

The intermediate structure 244 comprises the electrodes 230 arranged in a ring shape. At least one electrode ring 231 is provided, wherein the electrodes 230 are spaced apart at the electrode ring 231. In FIGS. 7a, 8 and 9 two electrode rings 231, i.e. inner and outer electrode rings, are provided, wherein the outer electrode ring 231 is encircled within the inner abrading edge 236a and the inner electrode ring 231 is encircled within the outer electrode ring 231. Each electrode ring 231 can provide at least one of operations of electroporation, microcurrent, iontophoresis, sonophoresis, galvanic, ultrasound, ultrasonic cavitation, acoustic cavitation, mesotherapy, radio frequency, and/or hot and cold therapies. The two electrode rings 231 can provide two different operations respectively. Therefore, two different sets of electrodes 230 are provided at the inner and outer electrode rings 231 respectively. Another electrode conductor 233 within the first electrode ring is extended toward the inner structure of the fluid delivery conduit 246 to meet with the aperture 224 to electrically charge any fluid ejected from the aperture. For example, one of the electrode rings 231 is to produce an electrical stimulant function, and another electrode ring 231 is to produce heat while the electrode 233 electrifies the fluids being pulled onto the skin.

It would be appreciated that one single electrode ring 231 is replaceably formed at the intermediate structure 244 as shown in FIG. 10. The single electrode ring 231 can be a sonic brush in FIG. 10.

Each of the electrode rings 231 and 231b is replaceable. Each electrode ring 231 and 231b has a latch 231a extended from the electrode ring 231 and 231b wherein the latch 231a is guided through the latch slot 232a at the sidewall of the tip 204 to detachably couple the electrode ring 231 and 231b at the slanted skin applying surface of the tip 204.

A terminal 239 is provided at the handle 102 and electrically linked to the control circuit 138. When the tip 204 couples to the handle 102, the electrodes 230 at the intermediate structure 244 electrically contact with the terminal 239.

The inner structure 246 comprises a fluid delivery structure, wherein the fluid delivery structure comprises the fluid delivery tip 222 and vacuum entry port 226. The fluid delivery tip 222 has at least one aperture 224, wherein the aperture 224 is formed at the slanted skin applying surface of the tip 204. The vacuum entry port 226 is also formed at the slanted skin applying surface of the tip 204 and is located away from the aperture 224.

The intermediate structure 244 comprises an electrode terminal 233 extended toward the aperture 224 to electrify and charge the fluid when the fluid is ejected right at the aperture 244.

The inner structure 246 further comprises a plurality of fluid delivery walls 245 extended between the aperture 224 and the vacuum entry port 226 to form a fluid detouring path. When the fluid is ejected from the aperture 224, the fluid is guided and detoured along the fluid detouring path to the vacuum entry port 226. Therefore, the fluid detouring path will prolong the traveling distance of the fluid from the aperture 224 to the vacuum entry port 226.

In FIGS. 9 and 10 two fluid delivery walls 245 are extended from two opposite sides, i.e. first and second sides, of a boundary wall that partitions the inner structure 246 into two side sections and a mid-section. The boundary wall is the boundary of the inner structure 246. Therefore, the boundary wall is the wall between the inner structure 246 and the intermediate structure 244. One of the fluid delivery walls 245 is extended from the first side of the boundary wall toward the second side thereof to form a first cornering region. Another fluid delivery wall 245 is extended from the second side of the boundary wall toward the first side thereof to form a second cornering region. The aperture 224 and the vacuum entry port 226 are formed at the two side sections and are located at two ends of the fluid detouring path. Therefore, the fluid will travel from one side section to another side section through the mid-section, wherein the fluid will pass the first and second cornering regions. Preferably, the fluid delivery walls 245 are extended in parallel. Therefore, the fluid detouring path is a zigzag path that the fluid travels in a zigzag manner from the aperture 224 to the vacuum entry port 226. The structure of the fluid detouring path is shown in the new figure, FIG. 7A. As shown in this figure, the fluid travels from the aperture 224 up through the fluid delivery walls 245 to the vacuum entry port 226.

An additional vacuum entry port 226a is provided at the fluid detouring path between the aperture 224 and the vacuum entry port 226. The size of the additional vacuum entry port 226a is smaller than the size of the vacuum entry port 226. The additional vacuum entry port 226a will suck small amount of fluid first before the vacuum entry port 226 such the rest of fluid. Preferably, the additional vacuum entry port 226a is located right after the second cornering region.

In the preferred embodiment, the outer structure 242, intermediate structure 244, and the inner structure 246 are integrated with the tip 204 at the skin applying surface. Only the electrode rings 231 and 231b are replaceably attached to the intermediate structure 244. The abrasive media 236 is optionally placed at the outer structure 242. Without the abrasive media 236, the inner abrading edge 236a, outer abrading edge 236b, and connecting abrading edges 236c at the outer structure 242 can perform the abrading operation.

The device of the present invention basically uses the electric current to stimulate blood circulation to increase the absorption of the liquid, similar to how the skin absorbs more when exercising or sweating from heat, the pores are more permeable. The electric currents to be used do cause the similar effect of softening the pores to allow liquid to penetrate deeper under the skin.

FIG. 11 shows the alternative of the tip 204 has a slanted skin applying surface, wherein the inner structure 246, including the aperture 224, vacuum entry port 226 and fluid detouring path, is remained the same. Only the outer structure 242 and intermediate structure 244 are interchanged. The electrode ring 231 is formed at the outer structure 242 and the abrading structure 232 is formed at the intermediate structure 244.

FIG. 12 shows another alternative of the tip 204. The inner structure 246, including the aperture 224, vacuum entry port 226 and fluid detouring path, is remained the same. The electrode ring 231 is formed at the outer structure 242. The abrading structure 232 is formed at the intermediate structure 244. The modification in FIG. 12 is that the abrasive media 236 is placed at the abrading end portion 234 and is placed at the top surfaces of fluid delivery walls 245 to increase the abrading surface of the tip 204.

Another embodiment in FIG. 13 illustrates a modification of the tip 304 that detachably couples to the handle 102. The tip 304 is an electrode skin treating tip which comprises an electrode film 304a provided at the slanted skin applying surface for generating a specific electrical current such as of electroporation, microcurrent, iontophoresis, sonophoresis, galvanic, ultrasound, ultrasonic cavitation, acoustic cavitation; mesotherapy, radio frequency, and/or hot and cold therapies. The electrode film 304a can also be a light film for generating a specific light wave for skin treatment. The electrode skin treating tip 304 can be attached to the handle 102 after the multi-functional tip 204 is removed. Therefore, the multi-functional tip 204 and the electrode skin treating tip 304 are interchangeable. It is worth mentioning that when the electrode skin treating tip 304 is used, the fluid delivery will not turned off. Therefore, no aperture 224 and vacuum entry port 226 is formed at the electrode skin treating tip 304.

An embodiment in FIG. 14 illustrates a further modification of the tip 404 that detachably couples to the handle 102. The tip 404 is a micro-needle skin treating tip, which is also the multi-functional tip 204 to provide multiple functions. Similar to the multi-functional tip 204 in FIG. 7, the micro-needle skin treating tip 404 has a slanted skin applying surface, wherein the outer structure 242, intermediate structure 444, and the inner structure 246 are coaxial with each other and are formed at the slanted skin applying surface. The outer structure 242 of the tip 404 comprises the abrading structure 232. The inner structure 246 comprises the fluid delivery tip 222 and vacuum entry port 226. The difference between the multi-functional tip 204 and the micro-needle skin treating tip 404 is that the intermediate structure 444 comprises a micro-needle assembly 430 having a plurality of micro-needles 431 provided at the skin applying surface between the outer structure 242 and the inner structure 246.

The micro-needle assembly 430 further comprises a vibrator 432 supported in the tip 404. The vibrator 432 is connected to the control circuit 138 and is linked to the micro-needles 431. During operation, the vibrator 432 will generate vibration force to vibrate the micro-needles 431, so that the micro-needles 431 will drive to reciprocatingly move and puncture into the skin surface. The vibrator 432 can be a sonic vibrator to generate sonic wave to vibrate the micro-needles 431. Therefore, the micro-needle skin treating tip 404 provides a micro-needling treatment for skin complexion improvement, wrinkle reduction and face rejuvenation. The micro-needle skin treating tip 404 will repair skin damage from the sun, from acne, from injuries etc. So making tiny puncture wounds in your skin via the micro-needles 431, it stimulates the skin to produce collagen to repair the puncture wounds. The micro-needle assembly 430 further comprises a needle leveling adjustor 433 provided at the sidewall of the tip 404, wherein the level of the micro-needles 431 will be adjusted by the needle leveling adjustor 433 in order to adjust how deep the micro-needles 431 to be punctured into the skin surface.

FIG. 15 shows another alternative of the micro-needle skin treating tip 504. The micro-needle skin treating tip 504 has a slanted skin applying surface, wherein the outer structure 242, intermediate structure 544, and the inner structure 546 are coaxial with each other and are formed at the slanted skin applying surface. The outer structure 242 of the tip 504 comprises the abrading structure 232.

The intermediate structure 544 comprises the fluid delivery structure having an aperture 524, a vacuum entry port 526, and an additional vacuum entry port 526a.

The inner structure 546 further comprises a fluid delivery wall 545 extended between the aperture 524 and the vacuum entry port 526 to form a fluid detouring path. When the fluid is ejected from the aperture 524, the fluid is guided and detoured along the fluid detouring path to the vacuum entry port 526. Therefore, the fluid detouring path will prolong the traveling distance of the fluid from the aperture 524 to the vacuum entry port 526. The fluid delivery wall 545 is extended between two opposite sides of the boundary wall that partitions the intermediate structure 544 into a loop structure, wherein the aperture 524 and the vacuum entry port 526 are located at two ends of the fluid detouring path respectively, so that the fluid travels around the inner structure 546 from the aperture 524 to the vacuum entry port 526.

The inner structure 546 comprises a micro-needle assembly 530 having a plurality of micro-needles 531 provided at the skin applying surface within the inner structure 546. The vibrator 432 and the needle leveling adjustor 433 as disclosed in FIG. 14 will also be employed in the micro-needle assembly 530. So, the vibrator 432 will generate vibration force to vibrate the micro-needles 531, so that the micro-needles 531 will drive to reciprocatingly puncture into the skin surface. The level of the micro-needles 531 will be adjusted by the needle leveling adjustor 433 in order to adjust how deep the micro-needles 431 to be punctured into the skin surface.

The multi-functional tip 204, the electrode skin treating tip 304, and the micro-needle skin treating tips 404, 504 are interchangeable.

Although, the present invention has been discussed in considerable detail with reference to certain preferred embodiments, other embodiments are possible. Therefore, the scope of the appended claims should not be limited to the description of preferred embodiments contained herein.

While the embodiments and alternatives of the invention have been shown and described, it will be apparent to one skilled in the art that various other changes and modifications can be made without departing from the spirit and scope of the invention.

The invention claimed is:

1. A skin treatment device, comprising:
a handle;
a multi-functional tip detachably coupled to said handle;
wherein said multi-functional tip has a skin applying surface comprising a skin abrading structure, a first electrode ring, a second electrode ring and a fluid electrode terminal formed on said skin applying surface, wherein said second electrode ring is encircled within said abrading structure, wherein said first electrode ring is encircled within said second electrode ring;
a fluid delivery conduit and a vacuum conduit extending alongside each other within said handle;
wherein said fluid delivery conduit extends within said handle to communicate with at least one fluid delivery aperture on said skin applying surface of said multifunctional tip and said vacuum conduit extends within said handle to communicate with a vacuum entry port on said skin applying surface of said multifunctional tip;
wherein said fluid delivery conduit guides a flow of fluid to be delivered on said skin applying surface of said multifunctional tip through said at least one of said fluid delivery aperture for said fluid to be charged by said fluid electrode terminal and said vacuum entry port simultaneously evacuating used fluid and debris from a skin surface to said vacuum conduit to be discharged; and
wherein said first electrode ring and said second electrode ring generate different frequency outputs using one of electroporation microcurrent, iontophoresis, sonophoresis, galvanic, ultrasound, ultrasonic cavitation, acoustic cavitation, mesotherapy, radio frequency, and/or hot and cold therapies combined to stimulate multiple depths of said skin applying surface simultaneously.

2. A skin treatment device, comprising:
a handle structure;
an interior within said handle structure;
a fluid delivery conduit positioned within said interior of said handle structure;
a vacuum conduit positioned within said interior of said handle structure;
a single multi-functional tip structure detachably coupled to said handle structure;
said single multifunctional tip structure comprising a fluid delivery tip having at least one fluid delivery aperture and a vacuum entry port;
wherein said fluid delivery conduit extends alongside said vacuum conduit in said interior within said handle structure;
wherein said fluid delivery conduit extends within said interior of said handle structure to communicate with said at least one fluid delivery aperture and said vacuum conduit extends within said interior of said handle structure to communicate with said vacuum entry port;

wherein said single multi-functional tip structure has a skin applying surface comprising an outer structure, an intermediate structure, and an inner structure, wherein said outer structure, said intermediate structure, and said inner structure are coaxial with each other and are formed at said skin applying surface of said single multifunctional tip structure;

wherein said outer structure comprises a crown-shaped abrading structure formed from a plurality of connecting inner and outer abrading edges spaced apart from each other and having grooves configured to abrade a skin surface when said multifunctional tip is in contact with said skin surface;

wherein said inner structure comprises a plurality of fluid delivery walls extended between said at least one fluid delivery aperture and said vacuum entry port to form a fluid detouring path to prolong the traveling distance of said fluid from said at least one fluid delivery aperture to said vacuum entry port;

wherein when said single multifunctional tip contacts a skin surface, a simultaneous vacuum action of said vacuum entry port pulls said fluid from at least a container through to said at least one fluid delivery aperture to deliver said fluid to the skin surface;

wherein said intermediate structure comprises a first outer electrode ring and a second inner electrode ring and wherein said first outer electrode ring is encircled within an inner edge of said crown-shaped abrading structure and said second inner electrode ring is encircled within said first outer electrode ring;

a fluid electrode terminal extended toward said at least one fluid delivery aperture to electrify a fluid when said fluid is ejected at said at least one fluid delivery aperture;

wherein said first outer electrode ring and said second inner electrode ring of said intermediate structure and said fluid electrode terminal extended toward said at least one fluid delivery aperture are electrically linked to a terminal and a control circuit through said handle structure;

wherein said first outer electrode ring and said second inner electrode ring of said intermediate structure are configured to generate different electrical frequency outputs to stimulate, heat, or cool a skin at multiple depths when subject to microdermabrasion using said skin treatment device; and wherein said crown-shaped abrading structure of said single multi-functional tip, abrades and ablates the outermost surface layer of said skin surface wherein said outer structure, said intermediate structure, and said inner structure are functioning simultaneously in a synergistic action to increase the permeability and the transdermal pathway of said skin surface for a charged fluid to penetrate deeper through said skin surface to perform a microdermabrasion and treatment of said skin surface while said vacuum entry port simultaneously removes a used fluid and a skin debris from said skin surface.

3. The skin treatment device in claim 2 wherein said first outer electrode ring and said second inner electrode ring are configured to provide different operations of current to each other with at least one of said operations comprised of electroporation, microcurrent, iontophoresis, sonophoresis, galvanic, ultrasound, ultrasonic cavitation, acoustic cavitation, mesotherapy, radio frequency, and/or hot and cold therapies.

* * * * *